United States Patent [19]
Rader et al.

[11] Patent Number: 5,893,873
[45] Date of Patent: Apr. 13, 1999

[54] SURGICAL INSTRUMENT HAVING A HANDLE WITH A REMOVABLE, ROTATABLE TIP

[75] Inventors: R. Scott Rader, Baltimore; Alexander C. Walsh, Hunt Valley, both of Md.; Carl C. Awh, Brentwood, Tenn.; Eugene deJuan, Jr., Phoenix, Md.

[73] Assignee: Johns Hopkins University, Baltimore, Md.

[21] Appl. No.: 08/731,894

[22] Filed: Oct. 22, 1996

Related U.S. Application Data

[60] Provisional application No.60/005,795, Oct. 23, 1995.

[51] Int. Cl.[6] .................................................. A61B 17/32
[52] U.S. Cl. ............................................................... 606/205
[58] Field of Search ................................ 606/205–210, 606/167, 170, 171, 174, 175, 139, 142, 144

[56] References Cited

U.S. PATENT DOCUMENTS

| | | | |
|---|---|---|---|
| 4,165,745 | 8/1979 | Heifetz | 606/174 |
| 4,258,716 | 3/1981 | Sutherland | 128/318 |
| 4,433,687 | 2/1984 | Burke et al. | 606/174 |
| 4,598,711 | 7/1986 | Deniega | 128/326 |
| 4,644,651 | 2/1987 | Jacobsen | 30/251 |
| 4,760,848 | 8/1988 | Hasson | 128/340 |
| 4,873,979 | 10/1989 | Hanna | 606/210 |
| 4,938,214 | 7/1990 | Specht et al. | 606/206 |
| 4,955,887 | 9/1990 | Zirm | 606/107 |
| 5,184,625 | 2/1993 | Cottone, Jr. et al. | 128/751 |
| 5,250,056 | 10/1983 | Hasson | 606/151 |
| 5,282,806 | 2/1994 | Haber et al. | 606/139 |
| 5,282,813 | 2/1994 | Redha | 606/159 |
| 5,290,302 | 3/1994 | Pericic | 606/167 |
| 5,308,357 | 5/1994 | Lichtman | 606/205 |
| 5,368,605 | 11/1994 | Miller, Jr. | 606/170 |
| 5,370,658 | 12/1994 | Scheller et al. | 606/205 |
| 5,417,203 | 5/1995 | Tovey et al. | 128/4 |

*Primary Examiner*—Michael Buiz
*Assistant Examiner*—Vikki Trinh
*Attorney, Agent, or Firm*—Roylance, Abrams, Berdo & Goodman, L.L.P.

[57] ABSTRACT

A surgical instrument includes a handle having a pair of actuating wings and a removable instrument tip. The instrument tip is constructed to perform a surgical operation. The handle includes an axially movable slider actuated by the actuating wings which operate the instrument tip. A shaft extends through the handle and is coupled to the instrument tip so that rotation of the shaft rotates the tip without interfering with the axial movement of the slider. The gripping surface of the actuating wings have a rounded surface to allow limited rotational movement of the instrument in the user's hand. The gripping surfaces are inclined toward the instrument tip to resist the handle slipping from the user's hand during use in the near vertical orientation.

28 Claims, 3 Drawing Sheets

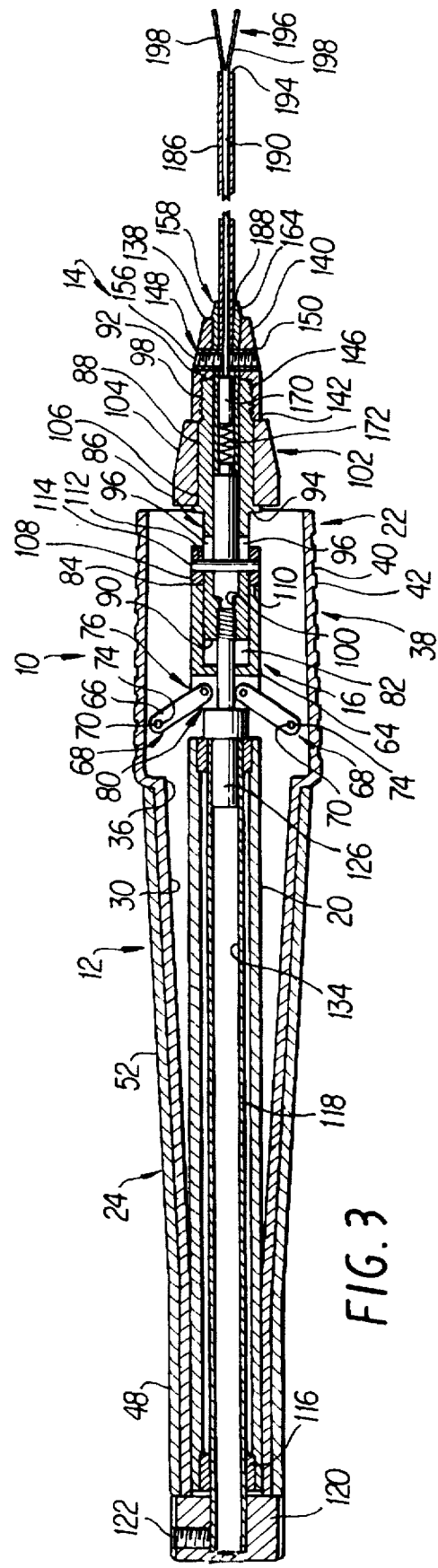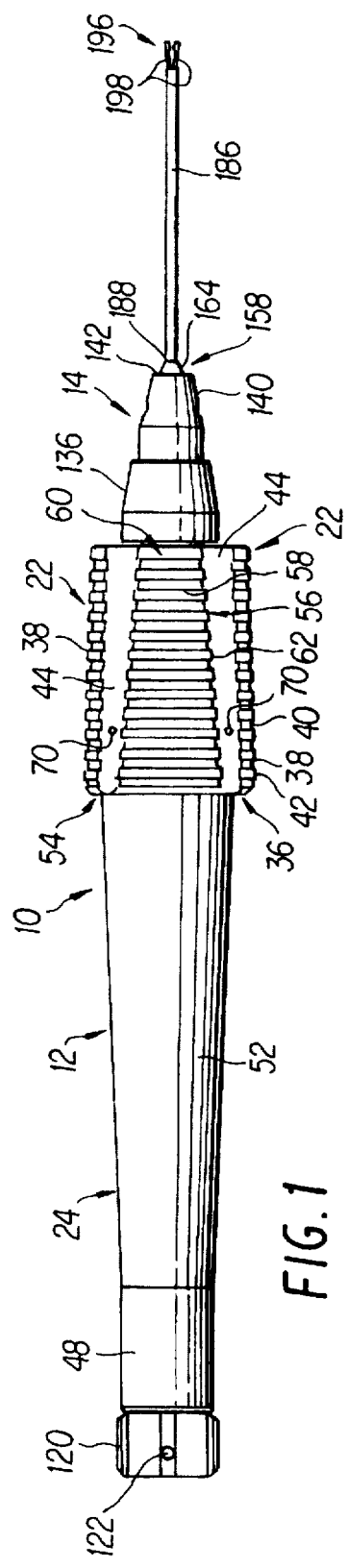

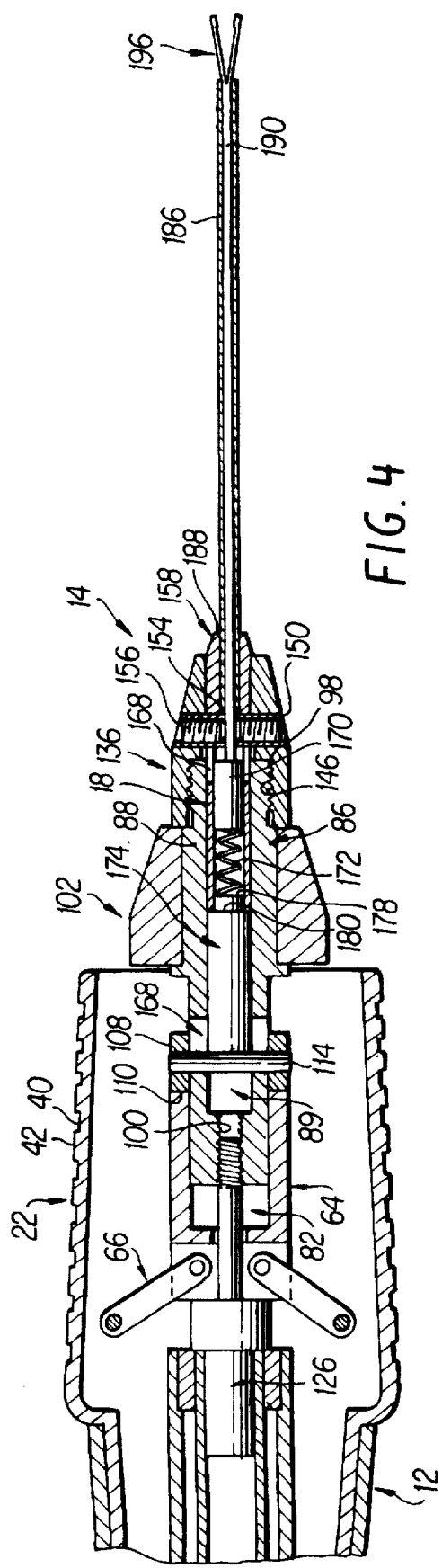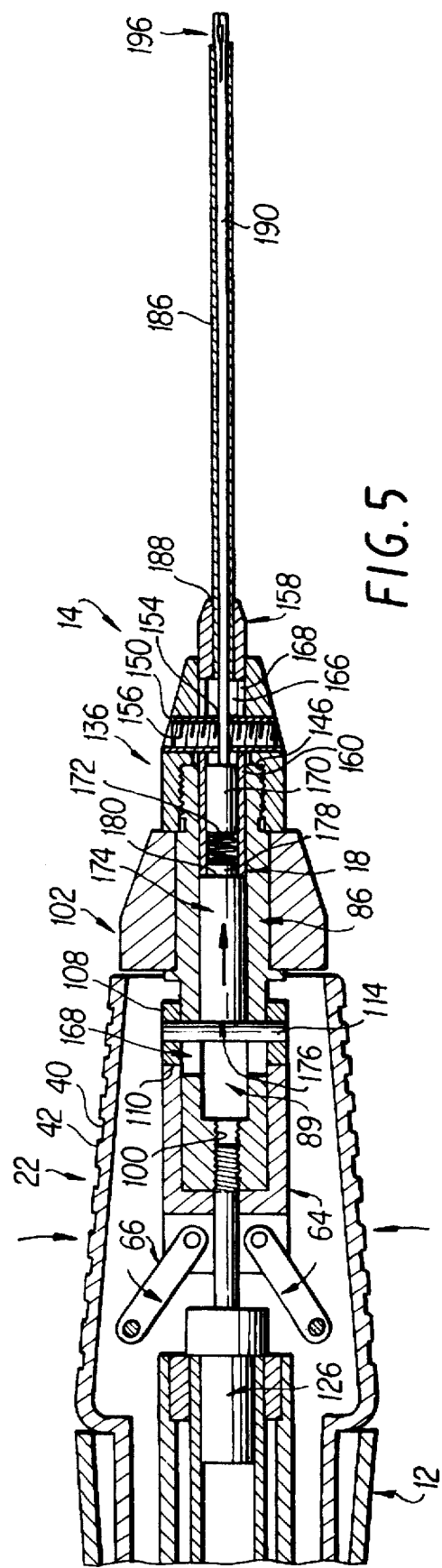

SURGICAL INSTRUMENT HAVING A HANDLE WITH A REMOVABLE, ROTATABLE TIP

This application claims the benefit under 35 U.S.C. § 119 (e) of U.S. provisional application Ser. No. 60/005,795 filed Oct. 23, 1995.

FIELD OF THE INVENTION

The present invention is directed to a hand held surgical instrument having a rotatably adjustable instrument tool tip. More particularly, the invention is directed to a surgical instrument having an ergonomically constructed handle to enable the surgeon to effectively grip and operate the instrument during use without interfering with rotation of the instrument tool tip.

BACKGROUND OF THE INVENTION

Numerous surgical instruments are known in the prior art for performing various surgical operations on small and delicate body parts. Ophthalmological instruments in particular are required to be very small while providing proper hand control over the instrument to effectively perform the surgical operation and to prevent damage to the tissue.

In microsurgery, such as in the eye, it is necessary to have an instrument which can enter the cavity of the eye and be manipulated easily within the eye at various angles with respect to the opening or incision and the operating surface without having to enlarge the opening Numerous devices have been proposed which have met with limited success for various reasons. Examples of these previous devices include finger operated scissors and forceps. Various surgical instruments have forceps or scissors which are not rotatably adjustable with respect to the handle and actuating mechanism. These devices are difficult to use at some angles with respect to the operating surface since the entire instrument must be rotated in the hand. Other surgical instruments which allow rotational movement of the instrument tip with respect to the handle do not lend themselves to easy rotational adjustment during use in surgery. Examples of these types of surgical instruments are disclosed generally in U.S. Pat. No. 4,258,716 to Sutherland, U.S. Pat. No. 4,955,887 to Zirm and U.S. Pat. No. 5,370,658 to Scheller et al.

A typical disadvantage of the previous surgical instruments is that the instruments can be difficult to manipulate in various rotational positions with respect to the plane of the actuating levers and fingers. To overcome this disadvantage, surgical instruments have been produced which have a rounded surface to enable the instrument to be rotated slightly in the surgeon's hand. These devices do not always provide proper or efficient actuation of the instrument following gross rotation within the handgrip. In addition, these surgical instruments typically have gripping surfaces which are wider at the distal end of the tool tip. Ophthalmological instruments, which are required to be used in a near vertical position, are difficult to grip with this type of handle. The inverted conical shape of the gripping surfaces allow the instrument to slip downwardly from the surgeon's fingers into the eye which can cause further damage to the eye. Although the surgical instruments can be provided with a slip resistant surface, it is difficult for the surgeon to grip the instrument when the instrument is covered with blood, mucus or other fluids encountered during surgery.

Another disadvantage of some of the prior surgical instruments is the ability of the actuating levers to pinch the surgeon's fingers or surgical gloves during actuation. This ultimately interferes with the surgeon's ability to operate the instrument and perform the surgical operation.

A further disadvantage of the previous surgical instruments is the actuating levers being positioned far from the tip of the instrument. The greater the distance the surgeon's fingers from the instrument tip, the greater any unintentional motions of the surgeon's fingers are amplified at the instrument tip. These prior devices do not permit the surgeon to grip the instrument sufficiently close to the instrument tip to minimize the motion amplification at the tip.

Accordingly, there is a continuing need in the art for surgical instruments which overcome the above-noted disadvantages of the prior surgical instruments.

SUMMARY OF THE INVENTION

The disadvantages and limitations of the previous surgical devices are obviated by the present invention while providing a surgical instrument which is convenient and easy to use. A primary aspect of the invention is to produce a surgical instrument which can be gripped effectively by the surgeon during use while permitting the surgeon to grip the instrument closer towards the instrument tip.

A further aspect of the invention is to provide a surgical instrument with a rounded gripping surface to allow the surgeon to make fine rotational adjustments of the instrument in the surgeon's fingers without interfering with the actuation of the instrument with the actuation of the instrument and without pinching the surgeon's gloves or fingers.

Another aspect of the invention is to provide a surgical instrument with an instrument tip which can be adjusted through a large rotational range to a selected position with respect to the instrument body by rotating a knob at the end of the handle opposite the instrument tip.

The surgical instrument of the invention basically comprises a handle and a removable instrument tip. The instrument tip can include a variety of tool tips such as, for example, forceps, scissors, and the like, which can be operated by the handle. The various instrument tips can be selectively attached to the handle as needed for the various phases of the surgical operation.

The handle includes at least one and preferably two opposing actuation wings which include a gripping surface. The gripping surface on each actuation wing has a rounded surface substantially concentric with the axis of the handle. The rounded surfaces allow a surgeon to rotate the handle slightly in the finger tips during use without diminishing the grip on the handle. The rounded surfaces of the gripping surfaces are in a plane oriented at an incline with respect to the center axis of the handle and converge toward the instrument tip to form a substantially frustoconical shape. The orientation of the gripping surfaces converging toward the instrument tip enhance the ability of the surgeon to grip the instrument when the instrument is oriented vertically.

The handle includes an actuation slider which is coupled to the actuation wings by a pair of lever arms so that actuation of the wings produces axial movement of the slider toward the instrument tip. The forward movement of the slider actuates the instrument tip by operating an actuation assembly in the instrument tip. A knob is connected to a shaft which extends through the handle and the slider and is coupled to the instrument tip. The knob which is located at the end of the handle opposite the instrument tip can be rotated to rotate the instrument tip with respect to the handle without interfering with the actuation of the tool.

These and other aspects of the invention are basically attained by providing a surgical instrument comprising: a hollow instrument handle having a longitudinal axis and first and second longitudinal ends; an instrument tool tip having a first end removably coupled to the second end of the handle, and a second end having a surgical tool for performing a surgical operation; an actuation slider mounted in the instrument handle for axial movement therein, the actuation slider having an axial bore extending therethrough; at least one manually operated actuation member operatively coupled to the actuation slider for producing the axial movement to the actuation slider; a follower member mounted in the handle and contacting the actuation slider for axial movement therewith; a rotation shaft means extending axially through the handle from the first end to the second end and through the actuation slider, the shaft means having a first end at the first end of the handle and a second end coupled to the instrument tip, wherein rotation of the shaft means within the handle causes rotation of the instrument tip.

The aspects of the invention are further attained by providing a surgical instrument comprising: a handle having a longitudinal axis, first and second axial ends, and an axial bore extending therethrough; an actuation slider mounted in the axial bore of the handle for limited axial movement therein, the actuation slider having an axial bore extending therethrough, and an axial face oriented toward the second end of the handle; at least one manually operated lever arm coupled to the actuation slider for causing the actuation slider to reciprocate axially in the handle; a rotatable shaft having a first end at the first end of the handle and a second end extending through the axial bore of the actuation slider, the shaft being fixed axially with respect to the handle, a core member having a first axial end coupled to the shaft for rotation therewith, follower means coupled to the core member for limited axial movement with respect to the core member, the follower means abutting the axial face of the actuation slider whereby axial movement of the actuation slider imparts axial movement to the follower means; an instrument tip removably coupled to the core member and including an instrument actuating member axially actuated by the follower means wherein axial movement of the follower means and actuating member actuates the instrument tip, wherein the shaft, core member and instrument tip are rotatable with respect to the handle.

Other aspects, advantages and salient features of the invention will become apparent from the following detailed description which, taken in conjunction with the annexed drawings, disclose preferred embodiments of the invention.

BRIEF DESCRIPTION OF THE DRAWINGS

Referring to the drawings which form a part of this original disclosure in which:

FIG. 1 is a top plan view of the surgical instrument in a preferred embodiment of the invention;

FIG. 3 is a cross-sectional view of the surgical instrument;

FIG. 4 is a partial cross-sectional view of the surgical instrument showing the actuator wings and the actuation slider in a first position and showing the instrument tip; and FIG. 5 is a partial cross-sectional view of the surgical instrument showing the actuation wings, slider and instrument in a second position.

DETAILED DESCRIPTION OF THE INVENTION

Figure 2:
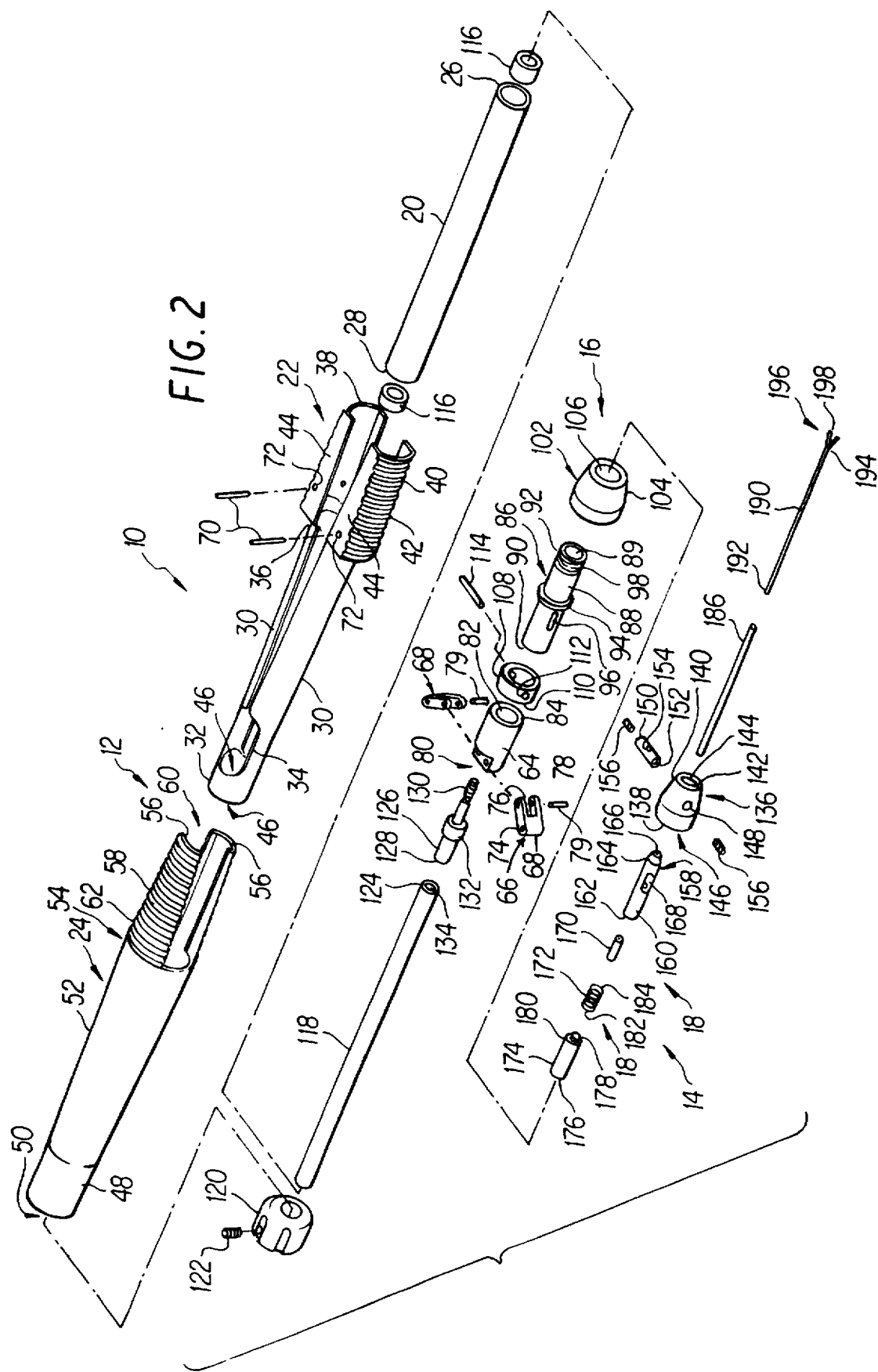
FIG. 2 is an exploded, elevated, perspective view of the surgical instrument.

The present invention is directed to a surgical instrument having a tool tip at one end which is actuated manually by the surgeon. More particularly, the invention is directed to a microsurgical instrument. The instrument tool tip is typically a set of forceps, scissors, or magnets, although other mechanically actuated surgical tools can be used. In embodiments, the surgical instrument is an intraocular device.

Referring to the drawings, the surgical instrument basically comprises a handle 12 and a removable instrument tool tip 14. A handle actuating assembly 16 is contained within the instrument handle 12. Instrument tool tip 14 includes a tool tip actuating assembly 18 as shown in FIGS. 2–5.

Referring to FIGS. 1 and 2, instrument handle 12 includes a fixed inner shaft 20, actuation wings 22 and an outer handle cover 24. Inner shaft 20 has a substantially tubular shape having an open first end 26 and an open second end 28. Actuation wings 22 are positioned to enclose inner shaft 20. Inner shaft 20 and actuation wings 22 are contained within outer handle cover 24 as shown in FIG. 3.

In preferred embodiments, actuation wings 22 are a unitary assembly defined by a pair of arms 30 joined to a cylindrical portion 32 at a first end. Arms 30 are coupled to cylindrical portion 32 by a spring portion 34 to form a pivot point of arms 30 with respect to cylindrical portion 32 and to bias arms 30 radially outward from the longitudinal axis of instrument 10 as discussed hereinafter in greater detail. Arms 30 swing inwardly in a generally arcuate path. Each arm 30 of actuation wings 22 include a second end 36 defined by an actuation member 38. Each actuation member 38 has a substantially circular outer gripping surface 40 having a plurality of ridges 42 providing a friction enhancing surface. Each actuation member 38 also includes a pair of opposite sides 44. Sides 44 are substantially planar and parallel to each other. Cylindrical portion 32 at the first end includes an axial bore 46 which slides over the first end of inner shaft 20. In preferred embodiments, bore 32 is dimensioned to friction fit over shaft 20 to couple actuation wings 22 to shaft 20.

Outer handle cover 24 has a substantially cylindrical first end portion 48 having an axial bore 50 dimensioned to receive cylindrical portion 32 of actuation wings 22. Bore 50 is also dimensioned to friction fit over cylindrical portion 32 to couple handle cover 24 to actuation wings 22. Handle cover 24 includes a body portion 52 having a substantially frustoconical shape which diverges from cylindrical end portion 48 toward a second end 54. End 54 is defined by a pair of tabs 56 extending axially from body 24. Each tab 56 has an outer non-slip surface 58 which together form a substantially frustoconical shape converging toward the second end 60 of handle 12. Non-slip surfaces 58 also include a plurality of ridges 62 to increase friction in the hands of the surgeon.

As shown in FIG. 1, handle 12 is assembled so that actuation members 38 of actuation wings 22 are positioned between tabs 56 of outer handle cover 24. Tabs 56 guide sides 44 of actuation members 38 so that actuation members 38 can pivot inwardly toward the axis of instrument 10 in an arcuate path. Tabs 56 effectively cover any open spaces between actuation members 38 to prevent pinching the surgeon's fingers during use and to prevent foreign material from interfering with the actuation of the instrument.

Gripping surfaces 40 on actuation members 38 have a substantially arcuate shape and are inclined toward second end 60. As shown in FIG. 1, gripping surfaces 40 are slightly inclined to define a substantially frustoconical cross-section converging toward the instrument tool tip 14.

The surgical instrument 10 when used for ophthalmological surgery is typically used in a near vertical position. The inclined gripping surfaces 42 and 58 produce a gripping reaction force substantially in the upward direction away from the instrument tip 14. When used in the vertical position, this reduces the risk of the surgical instrument from slipping downwardly into the ocular surface. The actuation wings 22 pivot inwardly in an arcuate path so that in the fully depressed position shown in FIG. 5, the angle of the gripping surfaces 42 become steeper, further promoting grip stability. Ridges 40 and 62 on gripping surfaces 40 and 48, respectively, in combination with the inclined surfaces, promote axial stability to the surgical instrument during use.

Referring to FIGS. 2 and 3, handle actuating assembly 16 includes an actuation slider 64 which reciprocates axially within handle 12 by actuating movement of actuating wings 22. An actuating lever 66 having a first end 68 is pivotally connected to each of the actuation members 38 by a pin 70. Pin 70 extends through apertures 72 on sides 44 and through an aperture 74 in lever 66. A second end 76 of actuation levers 66 include a pair of arms 78 which are pivotally coupled to a first end 80 of actuation slider 64 by pins 79. Actuation slider 64 includes a bore defining an axial passage 82 extending completely through the slider. A second end 84 of actuation slider 64 forms an annular shaped axial bearing face 84. As shown in FIGS. 4 and 5, depressing actuation wings 22 inwardly toward the axis of surgical instrument 10 produces a forward axial movement of actuation slider 64 toward second end 60 of handle 12.

A rotation core member 86 has a substantially cylindrical body portion 88 and a bore defining an axial passage 89 extending through body portion 88 from a first end 90 to a second end 92. An annular collar 94 extends radially outward from body portion 88 midway between first and second ends 90 and 92, respectively. Body portion 88 also includes an elongated slot 96 extending transversely through body portion 88. Slot 96 has a major dimension extending parallel to the axis of body portion 88. Second end 92 of body portion 88 includes an externally threaded portion 98 for coupling with instrument tool tip 14. The axial passage 89 in body portion 88 includes an internally threaded portion 100 at first end 90. A front cone 102 having a frustoconical surface 104 and an axial passage 106 is fitted onto body 88 at first end 90 to abut collar 94. In preferred embodiments, axial passage 106 is dimensioned to friction fit over body 88. Front cone 102 has a length so that when abutting collar 94, threaded portion 98 projects axially from cone 102.

An actuation follower 108 is slidably connected to core member 86. Actuation follower 108 has a substantially annular shape having a first annular surface 110 and apertures 112 on opposite sides and extending transversely through follower 108. Follower 108 is positioned on rotation core member 86 to align apertures 112 with elongated slot 96. A pin 114 is inserted through apertures 112 and elongated slot 96 to couple follower 108 to core member 86. Elongated slot 96 is dimensioned to permit limited axial movement of follower 108 with respect to core member 86.

Inner shaft 20 includes inner bearings 116 at first and second ends 26 and 28, respectively. A rotation shaft 118 extends through inner shaft 20 and is supported therein by bearings 116 as shown in FIG. 3. Rotation shaft 118 preferably extends from first end 48 of handle cover 24 and is coupled to a rotation knob 120. In the embodiment illustrated, rotation knob 120 includes a set screw 122 which is screwed inwardly to engage rotation shaft 118. Rotation shaft 118 includes a second end which is coupled to a rotation thrust bearing 126. Rotation thrust bearing 126 includes a first end 128 and a second threaded end 130. An annular collar extending radially outward from thrust bearing 126 is positioned midway between first and second ends 128 and 130, respectively. First end 128 of thrust bearing 126 can be coupled to rotation shaft 118 by any suitable means. In the embodiment illustrated, rotation shaft 118 includes an axial bore 134 which is welded to first end 128 of thrust bearing 126. In alternative embodiments, thrust bearing 126 and rotation shaft 118 can be coupled together by frictional engagement or cooperating threads.

Handle 12 is assembled by sliding rotation shaft 118 through bearings 116 in shaft 20 to extend from the second end of shaft 20. Rotation thrust bearing 126 is then attached to rotation shaft 118. Second end 130 of thrust bearing 126 extends into the axial passage 89 of core member 86. Threaded second end 130 of rotation thrust bearing 126 is threaded to internal threads 100 of core member 86. Actuation wings 22 and outer cover 24 are then positioned over inner shaft 20 as shown in FIG. 3. When assembled, depressing actuation wings 22 produces an axial movement of actuation slider 64 toward the instrument tool tip 14. As shown, actuation slider 64 and actuation levers 66 are rotationally fixed with respect to actuation wings 22. Rotation shaft 118, rotation thrust bearing 126 and rotation core 86 are coupled together whereby they are freely rotatable within handle 12 by rotation of knob 120. Actuation follower 108 being coupled to rotation core 86 by pin 114 rotates with rotation core 86. First annular surface 110 of actuation follower 108 defines a bearing surface against actuation slider 64. As shown, axial movement of actuation slider 64 causes axial movement of actuation follower 108 without inhibiting rotational movement of follower 108 and rotation core 86.

Instrument tool tip 14 includes a front cone 136 defining a head piece having a first end 138 and a frustoconical portion 140 converging toward a second end 142. An axial passage 144 extends through front cone 136 and includes an internally threaded portion 146 at first end 138 for coupling with threaded portion 98 of core member 86. A transverse passage 148 extends through front cone 136. A core holder 150 having an internally threaded passage 152 is fitted into transverse passage 148. Core holder 150 includes a transverse passage 154. Set screws 156 are threaded into the internal threaded passage 152 as shown in FIG. 3.

A tool tip slider 158 has a substantially cylindrical body 160, a first end 162 and a frustoconical second end 164. A bore defining passage 166 extends axially through body 160. An elongated slot 168 extends transversely through body 160. Tool tip slider 158 is positioned in axial passage 144 of front cone 136 to align transverse slot 168 with transverse passage 148. Core holder 150 is then inserted into transverse passage 148 passing through transverse slot 168 to retain slider 158 within front cone 136 while allowing limited axial sliding movement. A cylindrical spring bearing core 170 is placed in axial passage 166 of slider 158 from the first end 162 until spring core 170 engages core holder 150. A helical spring 172 is then placed in axial passage 166 to engage spring core 170. A cylindrical tool tip back plug 174 having a first axial face 176 and a cylindrical plug 178 extending axially from the second axial face 180 is inserted into axial passage 166. Plug 178 is dimensioned to friction fit in axial passage 166 to couple back plug 174 to slider 158. Spring 172 has a forward end 184 which engages spring core 170 in contact with core holder 150. Spring 172 has a rear face 182 abutting plug 178 of back plug 174 to bias tool tip slider 158 away from second surface 142 of front cone 136. A hollow hypodermic tube 186 is inserted into axial passage 166 of body 160 at second end 164 and is fixed thereto by suitable means such as, for example, soldering at 188.

Alternatively, tube 186 can be press fitted into axial passage 166. This arrangement of components enable the instrument tip to be shorter than conventional tips which enables the gripping surfaces of the actuation wings to be placed closer to the instrument tip.

A tool tip instrument rod 190 having a substantially cylindrical shape with a first end 192 and a second end 194 passes through tube 186. Second end 194 of rod 190 includes a tool 196 for performing a surgical operation. First end 192 of rod 190 passes through transverse passage 154 of core holder 150 and is positioned midway within passage 152. Set screws 156 in core holder 150 are tightened to clamp rod 190 in a fixed position with respect to front cone 136.

Tool 196 is a suitable surgical tool as known in the art. In the embodiment illustrated, tool tip 196 is integrally formed with rod 190 to define a pair of forcep jaws 198.

In operation, instrument tool tip 14 is coupled to handle 12 so that tool tip back plug 174 contacts pin 114 extending through follower 108. Depressing actuating wings 22 urges actuation slider 64 in an axial direction toward instrument tool tip 14. The axial motion of actuation slider 64 is transferred to actuation follower 108 which slides axially over core 86 with pin 114 riding in elongated slot 96. The axial motion of pin 114 is transferred to tool tip back plug 174 which urges tube 186 axially forward with respect to rod 190. As shown in FIGS. 4 and 5, depressing actuation wings 22 causes tube 186 to slide forward with respect to rod 190 to actuate tool 196. In the embodiment shown, forcep jaws 198 are spring biased outwardly so that sliding movement of tube 186 opens and closes forcep jaws 198. Instrument tool tip 14 is removably coupled to threaded portion 98 on core 86. In this manner, instrument tool tip 14 is rotatably mounted on handle 12 and can be selectively rotated by rotation knob 120. The angular position of instrument tool tip 14 can be selectively rotated 360° without interfering with the axial movement of actuation slider 64 and operation of the instrument. Rotation knob 120 at the first end of handle 12 can be adjusted during surgical operations and can be rotated by the surgeon or by an assistant.

The surgical instrument according to the invention is lightweight and easy to operate by the surgeon. The arrangement and operation of the tool tip enables the gripping surfaces of the actuation wings to be positioned close to the tool tip thereby providing increased stability in the hands of the surgeon. The inclined gripping surfaces on the actuation wings and handle further promote axial stability during use.

The closed side walls and rounded griping surfaces allow improved rotation and prevent interference by the actuation wing with the surgeon's gloves or fingers during actuation. The rotatable core allows 360° rotation of the tool tip without interfering with tool tip actuation.

The surgical instrument is manufactured from standard surgical grade materials such as, for example, stainless steel, aluminum and titanium. It is particularly desirable to manufacture the instrument from materials having good wear resistance for durability and temperature resistance to withstand autoclaving temperatures during sterilization.

While the present invention has been described by reference to specific embodiments, it should be understood that various modifications and changes of these embodiments can be made without departing from the scope of the invention as defined in the following claims.

What is claimed is:

1. A surgical instrument comprising:

a hollow instrument handle having a longitudinal axis and first and second longitudinal ends;

an instrument tip having a first end removably coupled to said second end of said handle, and a second end having a surgical tool for performing a surgical operation;

an actuation slider mounted in said instrument handle for axial movement therein, said actuation slider having an axial bore extending therethrough;

at least one manually operated actuation member operatively coupled to said actuation slider for producing said axial movement to said actuation slider;

a follower member coupled to said instrument tip and mounted in said handle and contacting said actuation slider for axial movement therewith;

rotation shaft means extending axially through said handle from said first end to said second end and through said actuation slider, said shaft means having a first end at said first end of said handle and a second end coupled to said instrument tip, wherein rotation of said shaft means within said handle causes rotation of said instrument tip.

2. The surgical instrument of claim 1, further comprising first and second actuation wings, each wing having a first end at said first end of said handle and a second end at said second end of said handle, said wings being pivotal about said first end in an arcuate path toward said axis of said handle;

a lever arm coupled to each actuation wing and to said actuation slider, wherein pivotal movement of said actuation wings cause axial movement of said actuation slider toward said second end of said handle.

3. The surgical instrument of claim 2, wherein said second end of said actuation wings comprise a substantially arcuate shaped gripping surface having a longitudinal axis which is inclined toward said second end of said handle at a first angle with respect to the axis of said handle, wherein said gripping surfaces together define a substantially frustoconical gripping surface.

4. The surgical instrument of claim 3, wherein a longitudinal axis of said first and second actuation wings in an actuated second position are inclined toward said second end of said handle at a second angle greater than said first-angle.

5. The surgical instrument of claim 2, wherein said handle further comprises first and second non-slip surfaces on opposite sides of said handle and being positioned adjacent said gripping surfaces of said actuation wings and having an axis inclined toward said second end of said handle, said first and second non-slip surfaces of said handle defining a substantially frustoconical surface.

6. The surgical instrument of claim 2, wherein said handle further comprises first and second surfaces on opposite sides of said handle and being positioned adjacent said actuation wings to substantially enclose an area between said actuation wings.

7. The surgical instrument of claim 1, wherein said instrument tip comprises a head piece having first and second ends and an axial bore therethrough, a hollow tube received in said axial bore and extending from said first end of said head piece, a rod mounted in said hollow tube for relative axial movement between said rod and said tube, and a spring biased slide member axially slidable within said head piece for producing said relative movement between said tube and rod, said slide member being acted upon by said follower member.

8. The surgical instrument of claim 7, wherein said rod is fixed to said head piece and said tube is fixed to said slide member for axial movement with respect to said rod.

9. The surgical instrument of claim 8, wherein said surgical tool is a pair of forcep jaws at said second end of said rod, said jaws being biased outwardly.

10. The surgical instrument of claim 1, further comprising a core member having a first end coupled to said second end of said rotational shaft means, said follower member having an axial bore receiving said core member, wherein said follower member is axially slidable on said core member.

11. The surgical instrument of claim 10, wherein said core member has an axial bore extending therethrough, and an elongated slot extending transversely therethrough, said elongated slot having a major axis oriented parallel to a longitudinal axis of said core member, and a pin extending through said elongated slot and coupled to said follower member for coupling said follower member to said core member and limiting said axial movement of said follower member on said core member.

12. The surgical instrument of claim 1, further comprising a knob attached to said first end of said shaft means for rotating said instrument tip.

13. A surgical instrument comprising:

a handle having a longitudinal axis, first and second axial ends, and an axial bore extending therethrough;

an actuation slider mounted in said axial bore of said handle for limited axial movement therein, said actuation slider having an axial bore extending therethrough, and an axial face oriented toward said second end of said handle;

at least one manually operated actuation wing coupled to said actuation slider for causing said actuation slider to reciprocate axially in said handle;

a rotatable shaft having a first end at said first end of said handle and a second end extending through said axial bore of said actuation slider, said shaft being fixed axially with respect to said handle, a core member having a first axial end coupled to said shaft for rotation therewith, follower means coupled to said core member for limited axial movement with respect to said core member, said follower means abutting said axial face of said actuation slider whereby axial movement of said actuation slider imparts axial movement to said follower means;

an instrument tip removably coupled to said core member and including an instrument actuating means acted upon by said follower means wherein axial movement of said follower means and actuating means actuates said instrument tip, wherein said shaft, core member and instrument tip are rotatable with respect to said handle.

14. The surgical instrument of claim 13, wherein said core member has a second axial end and an axial bore therein.

15. The surgical instrument of claim 14, wherein said core member has a pair of elongated slots on opposite sides thereof and extending transversely through said core member, said elongated slots having a major axis extending parallel to a longitudinal axis of said core member, said follower means having an axial bore, said core member being received within said axial bore of said follower means, and a pin coupled to said follower means and extending through said elongated slots in said core member for coupling said follower means to said core member and for providing limited axial movement of said follower means on said core member.

16. The surgical instrument of claim 13, further comprising a knob at said first end of said handle and being coupled to said shaft, wherein rotation of said knob rotates said instrument tip.

17. The surgical instrument of claim 13, wherein said instrument tip comprises a head piece having first and second ends and an axial bore extending therethrough, a hollow tube received in said axial bore and extending from said second end of said head piece, a rod mounted in said hollow tube, wherein said hollow tube moves with respect to said rod, and a slide member axially slidable within said head piece for producing relative movement between said rod and hollow tube, wherein said slide member is acted upon to said follower means.

18. The surgical instrument of claim 17, wherein said tube is coupled to said slide member for axial movement therewith, and said rod is fixed to said head piece.

19. The surgical instrument of claim 18, wherein said slide member has an elongated transverse slot and said head piece further comprises attachment means extending into said elongated transverse slot and engaging said rod to fix said rod to said head piece.

20. The surgical instrument of claim 13, further comprising first and second manually operated lever arms coupled to said actuation slider, and first and second spring biased actuation wings coupled to said first and second lever arms, respectively, said actuation wings having a first end being coupled to said handle and being pivotable inwardly about said first end of said handle from a first position toward said actuation slider to a second position.

21. The surgical instrument of claim 20, each said actuation wing comprising a second end having substantially arcuate shaped gripping surface, each said gripping surface having a longitudinal axis which is inclined toward said second end of said handle at a first angle with respect to the axis of said handle, wherein said first and second gripping surfaces together define a substantially frustoconical gripping surface.

22. The surgical instrument of claim 21, wherein said longitudinal axis of said first and second actuation wings in said second position are inclined toward said second end of said handle at a second angle greater than said first angle.

23. The surgical instrument of claim 20, wherein said handle further comprises first and second non-slip surfaces on opposite sides of said handle, each of said non-slip surfaces being positioned adjacent said gripping surfaces of said actuation wings and having an axis inclined toward said second end of said handle, said first and second non-slip surfaces of said handle defining a frustoconical surface.

24. A surgical instrument comprising:

an instrument handle having a longitudinal axis and first and second ends;

an instrument tool tip having a first end removably coupled to said second end of said handle and a second end having a surgical tool for performing a surgical operation, an actuation assembly disposed in said handle for actuating said instrument tool tip; and first and second manually operated actuation wings operatively coupled to said actuation assembly, each of said actuation wings having a gripping surface along a plane inclined with respect to said axis of said instrument handle and converging toward said second end, wherein said first and second gripping surfaces together define a substantially frustoconical shape.

25. The surgical instrument of claim 24, said instrument handle further comprising first and second non-slip surfaces adjacent said gripping surfaces of said actuation wings, each of said first and second non-slip surfaces of said instrument handle being formed in a plane converging toward said second end, wherein said non-slip surfaces together define a substantially frustoconical shape.

26. The surgical instrument of claim 24, further comprising rotation means at said first end of said instrument handle and being coupled to said instrument tool tip.

27. The surgical instrument of claim 26, wherein said actuation assembly includes an axial passage and said rotation means extends through said axial passage.

28. The surgical instrument of claim 24, wherein said actuation assembly comprises an actuation slider having an axial passage therethrough;

rotation means having a first end extending from said first end of said instrument handle and a second end extending through said axial passage in said actuation slider;

a core member coupled to said second end of said rotation means; and follower means engaging said actuation slider and being acted upon by said core member for limited axial movement, wherein said instrument tool tip is operated by said follower means.

* * * * *